United States Patent
Leukanech et al.

(10) Patent No.: US 7,070,578 B2
(45) Date of Patent: Jul. 4, 2006

(54) SURGICAL CASSETTE LATCHING MECHANISM

(75) Inventors: Kurt D. Leukanech, Laguna Nigel, CA (US); Daniel J. Wilson, Quali Valley, CA (US)

(73) Assignee: Alcon, Inc., Hunenberg (CH)

( * ) Notice: Subject to any disclaimer, the term of this patent is extended or adjusted under 35 U.S.C. 154(b) by 792 days.

(21) Appl. No.: 10/132,797

(22) Filed: Apr. 25, 2002

(65) Prior Publication Data
US 2003/0202894 A1    Oct. 30, 2003

(51) Int. Cl.
*A61M 1/00* (2006.01)
(52) U.S. Cl. .......................... 604/153; 604/33; 604/34; 292/48; 292/49; 292/201; 292/210; 292/304; 403/119; 403/113; 403/322.3; 417/477.13; 417/477.2
(58) Field of Classification Search ............... 417/360, 417/477.2, 474; 292/201, 48, 44, 49, 210, 292/304; 403/119, 113, 322.3, 312, 222.1, 403/222; 604/33, 32, 34, 250, 153 X
See application file for complete search history.

(56) References Cited

U.S. PATENT DOCUMENTS

| | | | |
|---|---|---|---|
| 3,756,752 A | 9/1973 | Stenner | |
| 4,256,442 A | 3/1981 | Lamadrid et al. | |
| 4,395,258 A | 7/1983 | Wang et al. | |
| 4,493,695 A | 1/1985 | Cook | |
| 4,626,248 A | 12/1986 | Scheller | |
| 4,627,833 A | 12/1986 | Cook | |
| 4,713,051 A * | 12/1987 | Steppe et al. ............... 604/30 | |
| 4,758,220 A | 7/1988 | Sundblom et al. | |
| 4,758,238 A | 7/1988 | Sundblom et al. | |
| 4,790,816 A * | 12/1988 | Sundblom et al. ............ 604/31 |
| 4,798,580 A | 1/1989 | DeMeo et al. | |
| 4,824,339 A | 4/1989 | Bainbridge et al. | |
| 4,904,168 A | 2/1990 | Cavoto et al. | |
| 4,927,411 A | 5/1990 | Pastrone et al. | |
| 5,125,891 A | 6/1992 | Hossain et al. | |
| 5,230,614 A | 7/1993 | Zanger et al. | |
| 5,267,956 A * | 12/1993 | Beuchat ....................... 604/30 |
| 5,324,180 A * | 6/1994 | Zanger ....................... 417/475 |
| 5,364,342 A * | 11/1994 | Beuchat et al. ............... 604/30 |
| 5,387,088 A | 2/1995 | Knapp et al. | |
| 5,445,506 A | 8/1995 | Afflerbaugh et al. | |
| 5,588,815 A | 12/1996 | Zaleski, II | |
| 5,676,530 A | 10/1997 | Nazarifar | |
| 6,053,543 A * | 4/2000 | Arabia et al. ............... 292/201 |
| 6,059,765 A | 5/2000 | Cole et al. | |
| 6,076,868 A * | 6/2000 | Roger et al. ................. 292/201 |
| 6,293,926 B1 | 9/2001 | Sorensen et al. | |
| 6,302,455 B1 * | 10/2001 | Huang ....................... 292/199 |

FOREIGN PATENT DOCUMENTS

| | | | |
|---|---|---|---|
| AU | 703803 | 7/1997 | |
| EP | 0 786 260 | 12/2001 | |
| GB | 2051455 A * | 5/1979 | |

* cited by examiner

*Primary Examiner*—Charles G. Freay
*Assistant Examiner*—Emmanuel Sayoc
(74) *Attorney, Agent, or Firm*—Jeffrey S. Schira

(57) ABSTRACT

A surgical system having a cassette latching mechanism having two pivoting latching rails. The rails are connected to a rotating latching wheel by spring-loaded latching arms. The latching wheel is connected to a motor by a latching pushbar. The cassette is pressed into the rails which initiates the rotation of the rails, which close onto the cassette. The motor next rotates the latching wheel, producing cam-like movement of the latching arms and thereby further pivoting the latching rails to the fully closed and locked position.

8 Claims, 3 Drawing Sheets

SURGICAL CASSETTE LATCHING MECHANISM

BACKGROUND OF THE INVENTION

This invention relates generally to the field of ophthalmic surgery and more particularly to a latching mechanism used in an ophthalmic surgery irrigation/aspiration system.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigation fluid that is injected into the surgical site.

The use of cassettes with surgical instruments to help manage irrigation and aspiration flows is well-known. One of the primary functions of the cassette is to control the aspiration level at the surgical site. The vacuum generating devices generally is contained within the surgical console and may be a venturi, diaphragm or peristaltic pump. This design requires that the cassette be held tightly in operative association with the console and in proper alignment. In addition, the cassette must be easy to install on and remove from the console.

Therefore, a need continues to exist for a surgical system that allows for a surgical cassette latching mechanism that holds the cassette tightly but allows for the easy installation and removal of the cassette.

BRIEF SUMMARY OF THE INVENTION

The present invention improves upon the prior art by providing a surgical system having a cassette latching mechanism having two pivoting latching rails. The rails are connected to a rotating latching wheel by spring-loaded latching arms. The latching wheel is connected to a motor by a latching pushbar. The cassette is pressed into the rails which initiates the rotation of the rails, which close onto the cassette. The motor next rotates the latching wheel, producing cam-like movement of the latching arms and thereby further pivoting the latching rails to the fully closed and locked position.

Accordingly, one objective of the present invention is to provide a surgical cassette latching mechanism.

Another objective of the present invention is to provide a surgical cassette latching mechanism having a pair of pivoting latching rails.

Another objective of the present invention is to provide a surgical cassette latching mechanism that securely holds the cassette within the surgical console.

Another objective of the present invention is to provide a surgical cassette latching mechanism that can be unloaded in a simple, automated manner.

These and other advantages and objectives of the present invention will become apparent from the detailed description and claims that follow.

DETAILED DESCRIPTION OF THE INVENTION

Figure 1:
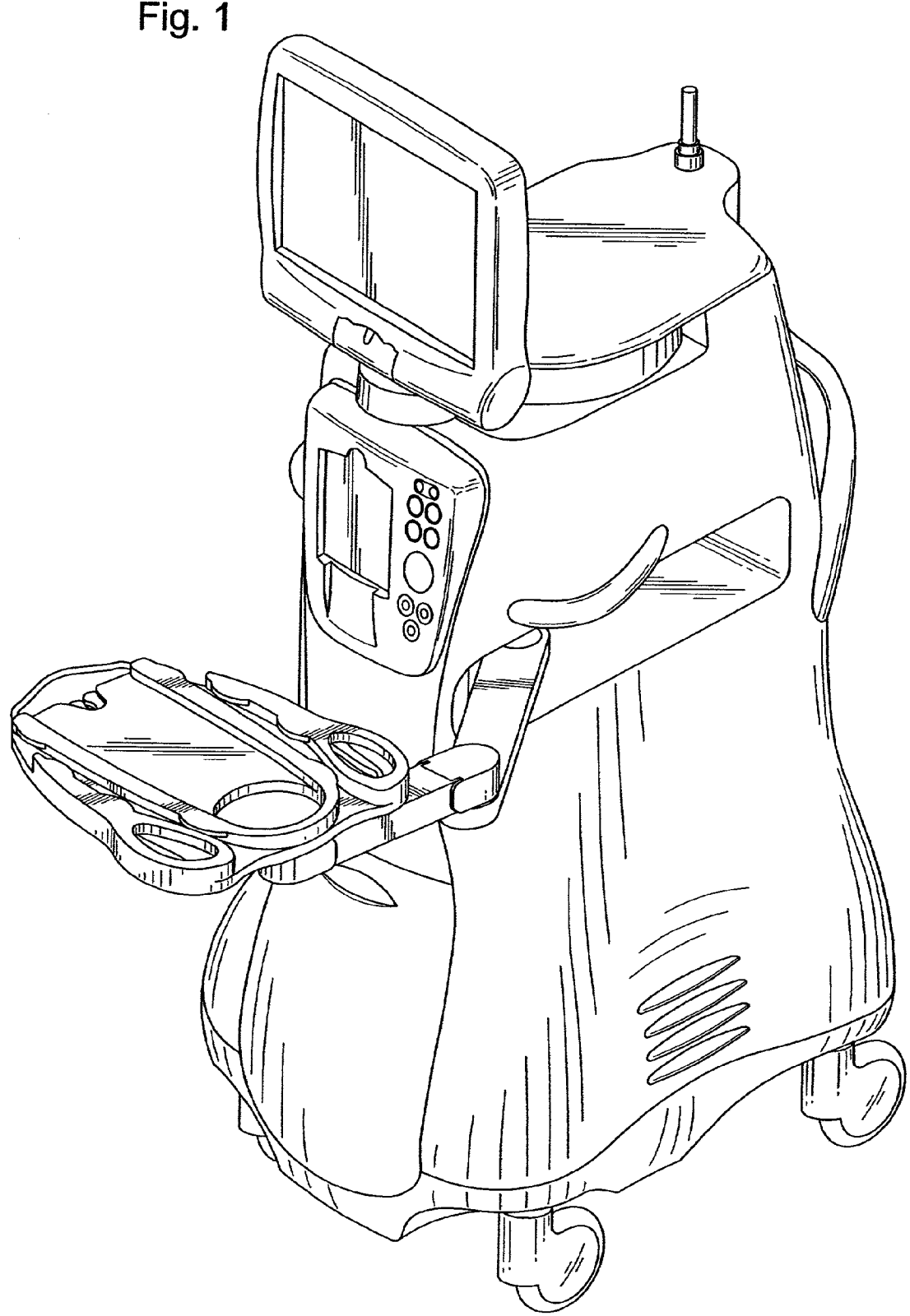
FIG. 1 is a perspective view of a surgical console that may be used with the latching mechanism of the present invention.
Figure 2:
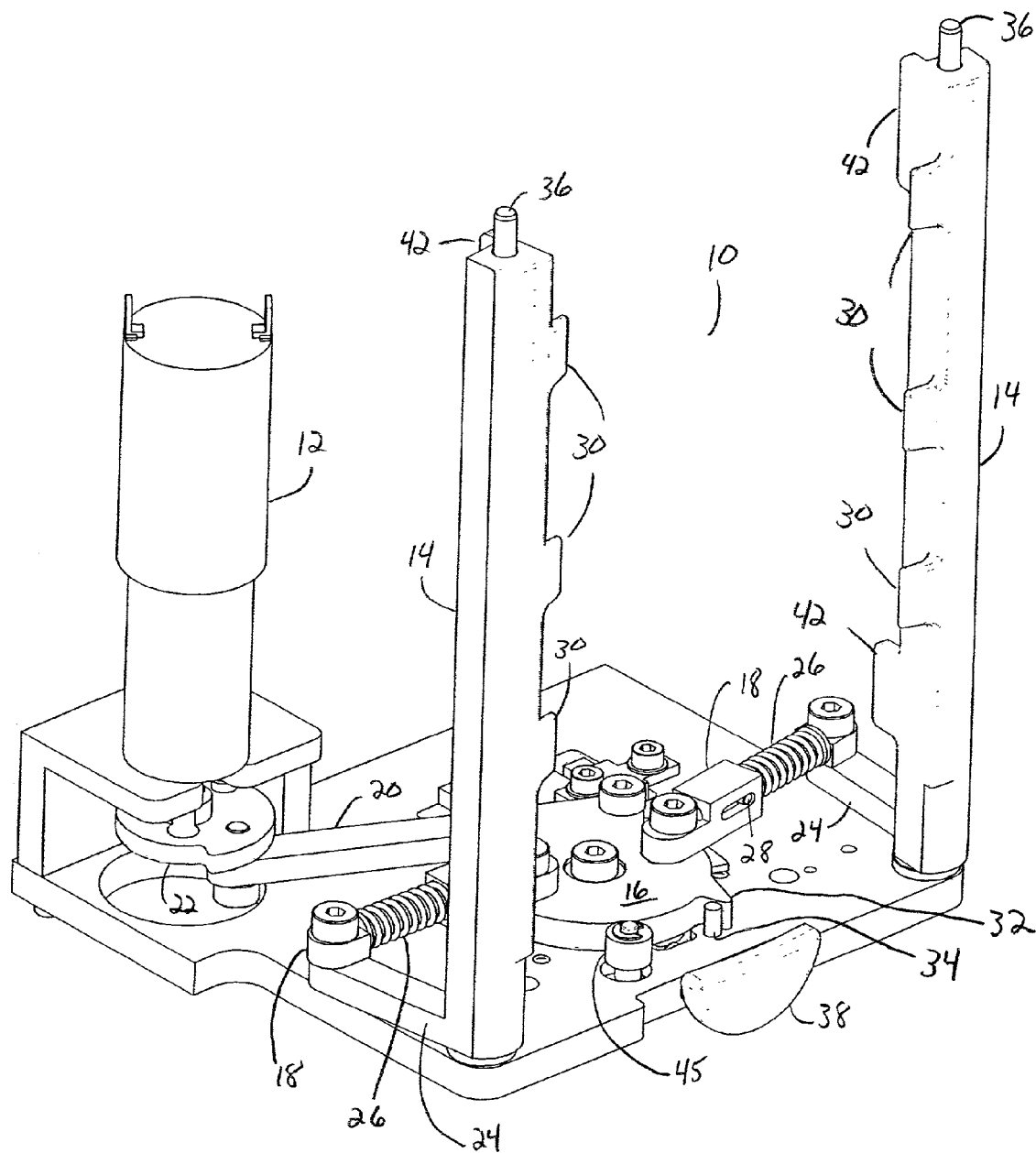
FIG. 2 is a top assembly view of the surgical cassette latching mechanism of the present invention.
Figure 3:
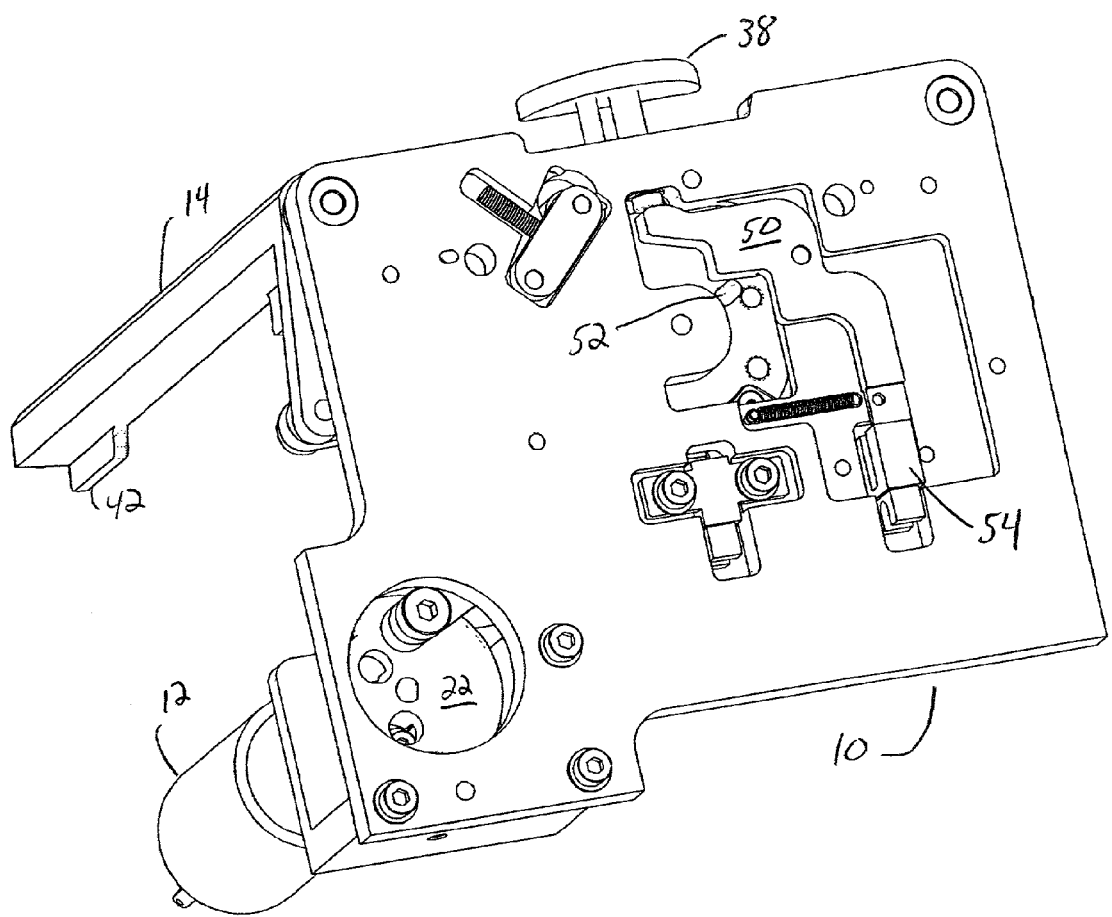
FIG. 3 is a bottom assembly view of the surgical cassette latching mechanism of the present invention.

Mechanism 10 of the present invention may be part of surgical console 100 illustrated in FIG. 1 and, as seen in FIG. 2, generally consists of motor assembly 12, rails 14, latching wheel 16 and latching arms 18. Motor 12 is eccentrically connected to latching wheel 16 by latching pushbar 20 and cam 22. Motor 12 preferably is a DC motor commercially available from a variety of sources and under appropriate software control. Latching arms 18 are connected on one end to latching wheel 16 and on the other end to pivot arms 24 formed on latching rails 14. Latching arms 18 are formed using springs 26 and reciprocating sockets 28 that prevent motor 12 from over-torquing rails 14. Wheel 16 contains a projection 32 that cooperates with stop pin 34 to prevent wheel 16 from over-rotating. Rails 14 contain a plurality of clamping fingers 30 and pivot about upper and lower pins 36. As best seen in FIGS. 2 and 3, mechanism 10 also contains manual latch release button 38 that cooperates with release mechanism 40 to provide a means for the manual release of rails 14. Release mechanism 40 contains unload bar 50 that pushes against pin 52 on the lower side of wheel 16. In the case of a loss of electrical power, pushing on button 38 causes unload bar 50 to push against pin 52, thereby causing rotation of wheel 16 to release the cassette in the manner discussed below. In addition, when power is available, button 38 is electrically connected to motor 12 by switch 54 so that a slight depression of button 38 pushes on unload bar 50, thereby activating switch 54 and causing motor 12 to rotate and release the cassette to the detent position discussed below.

Although mechanism 10 is suitable for use on a variety of cassettes, one preferred cassette is the cassette disclosed in U.S. Pat. No. 6,293,926 B1 (Sorensen, et al.), the entire contents of which being incorporated herein by reference. One surgical console suitable for use with mechanism 10 is illustrated in FIG. 1. The cassette disclosed in this patent requires that the cassette be held firmly against the pump mechanism contained in the surgical console. In use, mechanism 10 of the present invention operates by motor 12 pulling on pushbar 20 and thereby turning wheel 16 counterclockwise. Such rotation of wheel 16 pulls latching arms 18 inward and pivots rails 14 such that clamping fingers 30 pivot out and away from mechanism 10. The cassette can then be placed between rails 14, where it is held in place by fingers 30. A bump (not shown) on wheel 16 acts in cooperation with roller 45 to hold wheel 16 in place with fingers 30 in the open position. Insertion of the cassette presses the cassette against flippers 42, thereby causing rails 14 to rotate slightly. Rotation of rails 14 causes torque on wheel 16 sufficient to cause the bump to push back spring-loaded roller 45, thereby causing partial rotation of wheel 16 to a rest or detent position. This initial closure of mechanism 10 is caused entirely by the force of the insertion of the cassette. Once the cassette has been inserted and mechanism to is parked at the detent position, a sensor or switch is triggered, thereby energizing motor 12. To complete the latching of the cassette in mechanism 10, the direction of rotation of motor 12 is reversed so as to push on pushbar 20, thereby causing clockwise rotation of wheel 16. Clockwise rotation of wheel 16 pushes outwardly on latching arms 18 and causes rails 14 to pivot about pins 36 so that clamping fingers 30 pivot inwardly and draw the cassette toward mechanism 10. One skilled in the art will recognize that the amount of pivoting of rails 14 and the force with which rails 14 pivot may be adjusted to any suitable value by varying the length of pushbar 20 and or latching arms 18, the location of the attachment of pushbar 20 on cam 22 or heel 16 the location of attachment of latching arms 18 on wheel 16, the diameter of wheel 16, the length of pivot arms 24, the length of clamping fingers 30, the amount of rotation of motor 12 and/or any other suitable adjustment of the dimensions of the various components of mechanism 10. By way of example, mechanism 10 of the present invention may be operated using both motor 12 and manually by the user.

This description is given for purposes of illustration and explanation. It will be apparent to those skilled in the relevant art that changes and modifications may be made to the invention described above without departing from its scope or spirit.

We claim:

1. A surgical cassette latching mechanism, comprising:
   a) a motor having a cam;
   b) a latching wheel eccentrically connected to the motor by a pushbar so that rotation of the motor causes rotation of the latching wheel; and
   c) a pair of pivoting latching rails, connected to the latching wheel by a pair of latching arms so that rotation of the latching wheel causes pivoting of the rails thereby holding a surgical cassette between the rails.

2. The surgical cassette latching mechanism of claim 1 wherein rotation of the motor causes pivoting of the latching rails.

3. A surgical console, comprising: a cassette latching mechanism, the latching mechanism including a motor; a latching wheel connected to the motor by a pushbar so that rotation of the motor causes rotation of the latching wheel; and a pair of pivoting latching rails, the rails connected to the latching wheel by a pair of latching arms so that rotation of the latching wheel causes pivoting of the rails thereby holding a surgical cassette between the rails.

4. The surgical console of claim 3 wherein the cassette latching mechanism further includes latching rails containing a plurality of latching fingers.

5. The surgical console of claim 3 wherein the latching arms contain a spring.

6. The surgical console of claim 3 wherein the latching wheel contains a projection that cooperates with a stop so as to limit the rotation of the latching wheel.

7. The surgical console of claim 3 wherein the motor contains a cam and the pushbar is eccentrically connected to the cam.

8. The surgical console of claim 7 wherein rotation of the motor causes pivoting of the latching rails.

* * * * *